United States Patent [19]

Kamikado et al.

[11] 3,975,538
[45] Aug. 17, 1976

[54] MITICIDALLY ACTIVE COMPOSITIONS

[75] Inventors: Toshiya Kamikado, Ashiya; Takashi Kuragano, Amagasaki; Kazuo Konishi, Osaka; Yasuo Sato; Masayoshi Nagano, both of Kyoto, all of Japan

[73] Assignee: Takeda Chemical Industries, Ltd., Osaka, Japan

[22] Filed: June 16, 1975

[21] Appl. No.: 586,860

[30] Foreign Application Priority Data
June 14, 1974  Japan.................... 49-68501

[52] U.S. Cl................ 424/301; 260/455 B; 260/463
[51] Int. Cl.².................. A01N 9/20; C07C 69/96
[58] Field of Search.............. 260/463; 424/301

[56] References Cited
UNITED STATES PATENTS

| | | | |
|---|---|---|---|
| 3,804,874 | 4/1974 | Richter et al. | 260/463 X |
| 3,832,375 | 8/1974 | Itoh | 260/463 |
| 3,840,596 | 10/1974 | Richter et al. | 424/301 |

*Primary Examiner*—Joseph Paul Brust
*Attorney, Agent, or Firm*—Wenderoth, Lind & Ponack

[57] ABSTRACT

New miticidal compounds of the formula

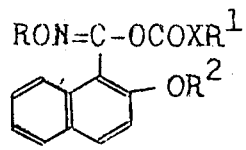

wherein R represents lower alkyl or lower alkenyl, $R^1$ and $R^2$ respectively represent lower alkyl and X represents oxygen or sulfur.

14 Claims, No Drawings

MITICIDALLY ACTIVE COMPOSITIONS

This invention relates to new compounds useful as miticides and their production.

Agricultural crops are infested by numerous species of mites, which cause severe damage. There is hardly any crop which is not damaged by some species of plant-feeding mites. For instance, the leaves and fruits of apples, mandarin oranges, apricots and pears are infested by the European red mite, citrus red mite and sweet cherry spider mite and Kanzawa spider mite, respectively.

Likewise, vegetables, such as cucumbers, cabbages, egg plants, watermelons, beans, as well as flowers, such as carnations, etc., and trees are infested by either two-spotted spider mite, clover mite, pseudocarmine mite or by the desert spider mite and seriously damaged thereby. However, most of the miticides currently available are of a narrow spectrum type, which are specifically toxic against only one or two species of the mites. Owing to their extremely high reproductivity, mites cause damage acceleratively in a short period of time, with a result that the repetition of applications of miticides and often of the same type of miticides becomes inevitable. This accelerates the appearance of mites resistant to these miticides through genetic mutation, which in turn reduces their effectiveness and eventually invalidates their miticidal value. Consequently, for the purpose of protecting agricultural products from the numerous species of mites, a broad-spectrum miticide, possessing a chemical structure different from that of any of the traditional miticides is needed.

Through research and experiments, the present inventors found that a group of new compounds represented by the following formula (I) are highly active against plant-feeding mites, low in toxicity against warm-blooded animals and fishes and do not exhibit any phytotoxicity on various agricultural crops. These compounds are found to be effective even against those mites which are resistant to known miticides, for instance, Benzomate (or Citrazon) (ethyl O-benzoyl-3-chloro-2,6-dimethoxybenzohydroxamate).

The present invention is the culmination of these findings. Thus, the main purpose of the present invention is to provide new compounds useful as miticides. Another purpose is to provide a process for the production of the new compounds. A further purpose is to provide new miticides containing the new compounds as the effective ingredients. A still further purpose will be readable on the following explanations.

The objective compounds of this invention are represented by the formula;

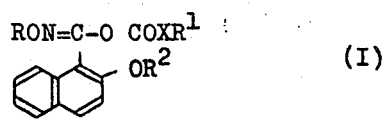

(I)

wherein R is lower alkyl or lower alkenyl, $R^1$ and $R^2$ respectively are lower alkyl and X is oxygen or sulfur.

The following compounds are the examples used as the miticides:

| Compound | R | X | $R^1$ | $R^2$ | Melting point(°C) |
|---|---|---|---|---|---|
| No. 1 | $C_2H_5$ | O | $CH_3$ | $CH_3$ | 93 – 96 |
| No. 2 | $C_2H_5$ | O | $C_2H_5$ | $CH_3$ | 61 – 63 |
| No. 3 | $C_2H_5$ | O | $n-C_3H_7$ | $CH_3$ | viscous & oily*1 |
| No. 4 | $C_2H_5$ | O | $i-C_3H_7$ | $CH_3$ | 58 – 60 |
| No. 5 | $C_2H_5$ | O | $n-C_4H_9$ | $CH_3$ | 39 – 41 |
| No. 6 | $C_2H_5$ | O | $i-C_4H_9$ | $CH_3$ | 58 – 59 |
| No. 7 | $C_2H_5$ | O | $sec-C_4H_9$ | $CH_3$ | 40 – 41 |
| No. 8 | $C_2H_5$ | O | $n-C_5H_{11}$ | $CH_3$ | viscous & oily*2 |
| No. 9 | $C_2H_5$ | O | $n-C_6H_{13}$ | $CH_3$ | viscous & oily*3 |
| No. 10 | $C_2H_5$ | O | $n-C_7H_{15}$ | $CH_3$ | viscous & oily*4 |
| No. 11 | $C_2H_5$ | O | $n-C_8H_{17}$ | $CH_3$ | viscous & oily*5 |
| No. 12 | $CH_2=CH.CH_2$ | O | $i-C_3H_7$ | $CH_3$ | 63 – 65 |
| No. 13 | $C_2H_5$ | S | $i-C_3H_7$ | $CH_3$ | 82 – 84 |
| No. 14 | $C_2H_5$ | S | $sec-C_4H_9$ | $CH_3$ | 77 – 79 |

*1 IR (Nujol), c=o 1770 cm$^{-1}$
*2 IR (Nujol), c=o 1770 cm$^{-1}$
*3 IR (Nujol), c=o 1770 cm$^{-1}$
*4 IR (Nujol), c=o 1770 cm$^{-1}$
*5 IR (Nujol), c=o 1770 cm$^{-1}$ The toxicity of these compounds is very low (mice; $LD_{50}$(per os) >300 mg./kg.).

These compounds can be produced through the reaction between the following two compounds, one of which is represented by the formula

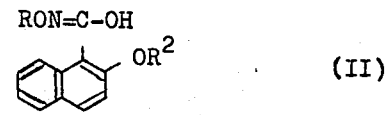

(II)

wherein R and $R^2$ have the same meanings as defined above and the other by the formula $$R^1X.COCl \qquad (III)$$

wherein $R^1$ and X have the same meanings as defined above.

For compound (III) the following are generally used: methyl chlorocarbonate, ethyl chlorocarbonate, propyl chlorocarbonate, isopropyl chlorocarbonate, butyl chlorocarbonate, isobutyl chlorocarbonate, secondary-butyl, chlorocarbonate, amyl chlorocarbonate, isoamyl chlorocarbonate, secondary-amyl, chlorocarbonate, hexyl chlorocarbonate, heptyl chlorocarbonate, octyl chlorocarbonate, methyl chlorothiocarbonate, ethyl chlorothiocarbonate, propyl chlorothiocarbonate, isopropyl chlorothiocarbonate, butyl chlorothiocarbonate, isobutyl chlorothiocarbonate, secondary-butyl chlorothiocarbonate, amyl chlorothiocarbonate, hexyl chlorothiocarbonate, heptyl chlorothiocarbonate, and octyl chlorothiocarbonate. The proportion of the two compounds (II) and (III) in the reaction is widely optional as long as it does not adversely affect the reacting process, but usually one part of compound (II) against one to 5 of compound (III) and, preferably one part of compound (II) against one to 1.5 parts of compound (III).

In general, it is preferable to have the two compounds react in a solvent; nevertheless, when necessary, the use of the solvent can be dispensed with. The following are generally used as the solvent: ethers, such as ethyl ether and dioxane; esters, such as ethyl acetate and butyl acetate; halogenated hydrocarbons, such as chloroform and methylenchloride; aromatic hydrocarbons, such as benzene and toluene; aliphatic hydrocarbons, such as n-hexane and cyclohexane; nitriles, such as acetonitrile and propionitrile; acid amides, such as dimethylformamide and N-methylpyrrolidone; sulfoxides, such as dimethylsulfoxide and tetramethylenesulfoxide; phosphoric amides, such as hexamethylphosphortriamide alcohols, such as methanol, ethanol, propanol and butanol; and water. Any of these solvents can be used singularly or in combination of two or more when required. For instance, when two solvents are used, their ratio can be one part of one against one to 10 parts of the other. When reaction commences, hydrogen chloride is produced as a by-product. Consequently, it is normally preferable to have the reaction take place in the presence of a base. As the base, any of the following organic tertiary amines can generally be used: aliphatic tertiary amines, such as triethylamine and tri-n-butylamine; aromatic tertiary amines, such as N,N-dimethylaniline and N,N-diethylaniline; heterocyclic compounds, such as pyridine and quinoline; diazabicyclic compounds, such as 1,8-diazabiclo-[5,4,0]-7-undecane (DBU) and 1,4-diazabicyclo-[2,2,2]-octane (DBO). Also, the following alkalis and alkaline earth metal compounds are generally used: metal hydroxides, such as sodium hydroxide, potassium hydroxide and calcium hydroxide; carbonates, such as sodium carbonate, potassium carbonate and magnesium carbonate; bicarbonates, such as sodium bicarbonate and potassium bicarbonate; organic acid salts, such as sodium formate and potassium acetate; alcoholates, such as sodium ethoxide and potassium t-butoxide; metal amides, such as sodium amide; hydrides, such as sodium hydride.

The base may be added to compound (II) prior to combining it with compound (III), or be added after the two compounds have been previously mixed. The quantity of the base to be used should be equivalent in mole to that of generating hydrogen chloride, or it may be 50 % in excess over mole of generating hydrogen chloride. An organic tertiary amine doubles as the base and the solvent, if an excessive amount is used. Moreover, when solvents such as dimethylformamide are used, or when the reaction is effected under heating, the addition of a base may be dispensed with.

The reaction will usually proceed smoothly under room temperature, but it can be accelerated when heated to a proper temperature. Also, in the instances where the reaction proceeds exothermically, it may be desirable to allow the reaction to proceed under cooling below room temperature. Usually, desirable results can be obtained, when the reaction temperature is controlled to range between room temperature and minus 20°C. The duration of the reaction may be suitably regulated by controlling the reaction temperature and it ranges between several minutes and several days, preferably between several 10 minutes and several hours. Other factors affecting the reaction conditions are the reacting compounds, solvent and base chosen, etc.

Compound (I), the product, thus obtained, can be isolated and purified by per se established procedures such as concentration, concentration under reduced pressure, distillation, fractional distillation, solvent extraction, pH adjustment, distribution, crystallization, recrystallization and chromatography. Solvents such as cyclohexane and benzene are generally used for recrystallization.

Compounds of Formula (I) in either purified or impurified state may be used undiluted as miticide, either singularly or in combination, to suit the purpose of its usage. Also, it can be used either dissolved or dispersed in a liquid carrier, such as solvents. It can also be mixed with or be absorbed by a solid carrier, such as diluting or extending agents. Moreover, when desirable, there are added to such preparations additives such as emulsifying, dispersal, suspension, spreader, absorbing, penetrating, wetting, viscosity-improving and stabilizing agents can be added. As miticides the compound (I) can be used as oily, emulsified, water-dispersible, powdered, granular, tablet or sprayable preparations.

Solvents suitable for use with this invention are as follows: alcohols, such as methyl alcohol, ethyl alcohol and ethylene glycol; ketones, such as acetone and methyl ethyl ketone; ethers, such as dioxane, tetrahydrofuran and cellosolve; aliphatic hydrocarbons, such as gasoline, kerosene, fuel oil and machine oil; aromatic hydrocarbons, such as benzene, toluene, xylene, solvent naphtha and methyl naphthalene; halogenated hydrocarbons, such as chloroform and carbon tetrachloride; acid amides, such as dimethylformamide; esters, such as ethyl acetate, butyl acetate and glycerine ester of aliphatic acid; and nitriles, such as acetonitrile. One or a combination of two or more of these solvents may be used.

As diluting or extending agents, powdered vegetable matters, such as soybean, tobacco, walnut, wheat and wood; powdered mineral matters, such as clays (e.g. kaolin, bentonite and Japanese acid clay), talcs (e.g. talcum powder and pagodite), silicas (e.g. diatomite and mica), as well as alumina, silica gel, powdered sulfur and activated carbon may be used, either singularly or in combination.

Also, if needed, for emulsifying, spreading, penetrating, dispersing and solubility-improving agents, such surfactants can generally be utilized as soaps, sulfuric ester of higher alcohols, alkylsulfon acid, alkylallylsulfon acid, quaternary ammonium salt, oxyalkylamine, aliphatic acid ester, polyalkyleneoxides and anhydrosorbitols. Furthermore, when needed, there are employed such matters as casein, gelatin, starch, alginic acid, agar, polyvinyl alcohol, turpentine, bran oil, bentonite, cresol soap and aluminum hydroxide.

Furthermore, these miticide compositions may be mixed and used in combination with other types of insecticides (organo-chlorine compounds, organophosphorous compounds, carbamate compounds and insecticides of plant origin), other types of miticides, as well as nematocides, bactericides, herbicides, plant-growth regulators, synergists, attractants, repellants, fragrances, plant nutritions and fertilizers.

The dosage, prescribed for the use of the miticide of this invention, when used singularly, and the proportion thereof, when used in combination with other types of insecticides, etc., will vary according to the species of mites to be controlled, their stages of growth, condition of infestation, method of cultivation of the infested crops, the time and conditions under which the application is to be made, methods of application and the economy of application. However, when used in an emulsion or wettable powder, the recommended effective dosage would range between 10 and 90 % of the preparation, and when used in oil or powder, it would range between 0.1 and 10 %. The dosage may be varied to conform to the purpose of usage. When the preparation is in the form of an emulsion or wettable powder, it better be diluted with the proper amount of water and the like prior to application.

This invention's outstanding feature is that, while effectively eradicating mites, it is nontoxic to either man, beasts or beneficial animals.

Experiments and working examples are given below. Compounds (I), (II) and so forth refer to compounds of Formulas (I), (II), etc. mentioned earlier.

EXAMPLE 1

2.45 g. of ethyl 2-methoxy-1-naphthohydroxamate was dissolved in a solution of 30 ml. of chloroform, to which was added 1.0 g. of sodium hydroxide in a 40 % aqueous solution, and 0.3 ml. of triethylamine. 1.8 g. of ethylchlorocarbonate dissolved in 2.0 ml. of chloroform (alcohol free) was added dropwise to the mixture at a temperature ranging between $-5°$ and $-10°C$. Then, it was stirred for 2 hours at $0°C$, followed by a stirring for 30 minutes at room temperature to bring the reaction to completion. The layer of chloroform solution was separated and washed with 10 ml. of sodium hydroxide (5 % aqueous solution) and water, dried over sodium sulfate and evaporated to dryness under reduced pressure to produce crystals, which were recrystallized from cyclohexane to produce 2.0 g. (a yield of 81.6 %) of white crystals, consisting of ethyl O-ethoxycarbonyl-2-methoxy-1-naphthohydroxamate (compound No.2) with a melting point ranging between $61°$ and $63°C$.

Elemental analysis (%) for calculated $C_{17}H_{19}NO_5$: C, 64.46; H, 6.04; N, 4.42; Found: C, 64.46; H, 5.96; N, 4.38. IR (Nujol): $c=O$, 1760 cm$^{-1}$.

EXAMPLE 2

To 30 ml. of chloroform, 2.45 g. of 2-methoxy-1-naphthohydroxamate, 1.0 g. of sodium hydroxide (40 % aqueous solution) and 0.3 ml. of triethylamine were added. At a temperature ranging approximately between $-5°$ and $-10°C$, 1.40 g. of isopropyl chlorothio carbonate dissolved in 10 ml. solution of toluene was added dropwise to the mixture. This was then stirred at a temperature of $9°C$ for 2 hours, followed by stirring for 30 minutes at room temperature to bring the reaction to completion. The layer of chloroform solution was separated and washed with 20 ml. of sodium hydroxide (10 % aqueous solution), then with water twice, and evaporated under reduced pressure to produce crystals, which were recrystallized from cyclohexane to yield 2.2 g (a yield of 62.5 %) of ethyl O-isopropylthiocarbonyl-2-methoxy-1-naphthohydroxamate with a melting point ranging between $82°$ and $84°C$.

Elemental analysis (%) calculated for $C_{18}H_{21}NSO_4$: C, 62.22; H, 6.09; N, 4.03; S, 9.23; Found: C, 62.35; H, 6.15; N, 3.88, S, 9.12. IR (Nujol): $c=O$, O, 1730 cm$^{-1}$.

EXAMPLE 3

Compound No.2, 40 parts; lignin sodiumsulfonate 5 parts; polyoxythelenealkylallylether, 5 parts; and powdered clay, 50 parts; mixed as a wettable preparation.

EXAMPLE 4

Compound No.3(or No.4), 20 parts; xylene, 70 parts; and polyoxyethylenediphenylether, 10 parts; mixed as an emulsion preparation.

EXAMPLE 5

Compound No.7, 5 parts; and powdered clay, 95 parts; mixed as a powder preparation.

EXAMPLE 6

Compound No.13, 5 parts; finely powdered bentonite and clay, 95 parts; mixed, kneaded and finished as a granular preparation.

Experiment 1 (miticidal test)

In this experiment, approximately 50 larvae and adults of the citrus red mite, *Panonychus citri* were first released on the leaves of a young lemon tree, with about 10 leaves, growing in a pot (9 cm in diameter). Various compounds of Formula (I) in an emulsion as prepared in Example 4 were each diluted to 200 ppm in water (with 3,000 parts of spreader agent added). Two days later, each potted plant was sprayed with 20 cc of one of these preparations with a spray gun (under 1 kg/cm$^2$ pressure, 80 cm distance from the plant) in a spray chamber. After the spraying, the pots were placed in a air-conditioned greenhouse (28°C) for 10 days, the number of mites and eggs surviving on the leaves counted. The effectiveness of the applications was evaluated by the following evaluation criteria and are given in Table 1 below.

Criteria for evaluating effectiveness:

| Mortality of mites and eggs (%) | Evaluation |
|---|---|
| 100 % | +++ |
| 90 – 99 % | ++ |
| 50 – 89 % | + |
| 49 % or less | − |

Table 1

| Compounds tested | Evaluation |
|---|---|
| No. 1 | ++ |
| No. 2 | ++ |
| No. 3 | +++ |
| No. 4 | +++ |
| No. 5 | +++ |
| No. 7 | +++ |
| No. 8 | ++ |
| No. 9 | ++ |
| No. 10 | ++ |
| No. 11 | ++ |
| No. 12 | ++ |
| No. 13 | +++ |
| No. 14 | ++ |
| Control No. 1: ethyl O-benzoyl-2-methoxy-1-naphthohydroxamate | − |
| Control No. 2: ethyl O-(4-methylbenzoyl)-2-methoxy-1-naphthohydroxamate | − |
| Unsprayed | − |

Note: The compounds as the control are disclosed in Japanese Patent Publication 18858/1974 as effective against a certain type of mites.

EXPERIMENT 2

In this experiment, 1 day after approximately 50 female adults of the two-spotted spider mite, *Tetranychus urticae*, were released on the leaves of a seedling pea plant (5 days after germination), growing in a pot (9 cm in diameter), the plant was sprayed with emulsion compounds of Formula (I) as prepared in Example 4 diluted to 500 ppm in water; each plant was sprayed with 20 cc of one of the preparations, as in Example 1. After spraying the pots were placed in a air-conditioned greenhouse (28°C) for 2 days. Then, the number of surviving mites were counted and the effectiveness was evaluated as in Example 1. The results are given in Table 2 below.

Table 2

| Compounds tested | Evaluation |
| --- | --- |
| No. 1 | ++ |
| No. 3 | ++ |
| No. 4 | +++ |
| No. 5 | ++ |
| No. 6 | ++ |
| No. 7 | ++ |
| No. 8 | +++ |
| No. 9 | ++ |
| No. 10 | ++ |
| No. 11 | ++ |
| No. 12 | +++ |
| No. 14 | ++ |
| Control No. 1: ethyl 0-benzoyl-2-methoxy-1-naphthohydroxamate | − |
| Control No. 2: ethyl 0-(4-methylbenzoyl)-2-methoxy-1-naphthohydroxamate | − |
| Unsprayed | − |

EXPERIMENT 3

In this experiment, one day after approximately 50 female adults of the Kanzawa spider mite, *Tetranychus kanzawai*, were placed on the leaves of a seedling of the pea plant (5 days after germination), growing in pots (9 cm in diameter), the plant was sprayed with emulsion of the compound of Formula (I), diluted to 500 ppm in water. Each plant was sprayed with 20 cc of one of the preparations, as in Example 3. And the effective thereof was evaluated as in Example 1. The test was repeated three times. The results are shown in Table 3 below.

Table 3

| Compounds tested | Evaluation |
| --- | --- |
| No. 3 | ++ |
| No. 4 | ++ |
| No. 5 | ++ |
| No. 12 | +++ |
| Control No. 1: ethyl 0-benzoyl-2-methoxy-1-naphthohydroxamate | − |
| Control No. 2: ethyl 0-(4-methylbenzoyl)-2-methoxy-1-naphthohydroxamate | − |
| Unsprayed | − |

EXPERIMENT 4 (OVICIDAL TEST)

In this experiment, 20 female adults of the citrus red mite were released on the leaves of the potted trifoliate orange (15 cm in height). The pots were then placed in a air-conditioned greenhouse (28°C) for 2 days. Then the adults were removed from the plant and the eggs laid on the leaves were subjected to the ovicidal test. The number of the eggs on each plant was counted prior to the chemical application. As in Example 1, each of the emulsion compounds as prepared in Example 4 was diluted to 500 ppm in water. 20 cc of each compound was sprayed on one of the plants. After spraying, the pots were returned to the air-conditioned greenhouse and kept there for 7 days. Then, by microscopic inspection, the numbers of unhatched eggs, the larvae which died after hatching, and the surviving larvae, respectively, on each plant were counted. The ovicidal effectiveness on the mites' eggs was rated by the standards of Example 1. The test was repeated three times; the results are shown in Table 4 below.

Table 4

| Compounds tested | Evaluation |
| --- | --- |
| No. 2 | ++ |
| No. 3 | ++ |
| No. 4 | +++ |
| No. 5 | ++ |
| No. 6 | ++ |
| No. 8 | ++ |
| No. 9 | ++ |
| No. 10 | +++ |
| No. 12 | +++ |
| Control No. 1: ethyl 0-benzoyl-2-methoxy-1-naphthohydroxamate | − |
| Control No. 2: ethyl 0-(4-methylbenzoyl)-2-methoxy-1-naphthohydroxamate | − |
| Unsprayed | − |

EXPERIMENT 5

100 female adults of citrus red mite which show resistance to citrazon were released on the leaves of the potted trifoliate orange (The pot: 9 cm in diameter). 20 cc each of the emulsions 100 prepared in Example 4, of compound No.4 and citrazon (mentioned before) for comparison of different concentrations was sprayed on one of the pots. After spraying the pots were kept in a kasten for 2 days and from the number of the surviving mites the death rates were calculated. The test was repeated twice and the results are shown in Table 5.

Table 5

| Concentration (ppm) | Death rate % | |
| --- | --- | --- |
| | Compound No. 4 | Citrazon |
| 12.5 | 25.3 | 19.5 |
| 25.0 | 44.3 | 25.8 |
| 50 | 47.0 | 40.6 |
| 100 | 51.2 | 40.5 |
| 200 | 93.5 | 43.5 |
| 400 | 100 | 68.0 |
| Unsprayed | 0 | |

EXPERIMENT 6

The control test of powdery mildew of apple plant.

The seedlings of the apple (*Malus pumila miller var. domestica* Schneider *f. Rall's Janet*) in their 7 to 10-leaf stage were employed. The pathogenic fungi on diseased leaves of an apple plant were dusted over the tops of the seedlings which, then, were kept in a green house. After 2 days, the fungicidal solutions prepared in the same manner as Example 4 were sprayed in sufficient volume. After the application, the seedlings were further grown in a green house. After 7 and 14 days, the percent area of the lesion was investigated. The test was conducted in duplicate for each group.

Table 6

| Test substance | Concentration (ppm) | Percent area of the lesion (%) | | phyto toxicity |
| --- | --- | --- | --- | --- |
| | | 7 days | 14 days | |
| Compound No.4 | 125 | 6.4 | 11.3 | − |
| Unsprayed | − | 22.3 | 56.9 | |

What we claim is:
1. A compound of the formula

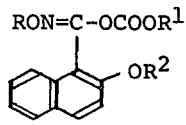

wherein R represents lower alkyl or lower alkenyl and $R^1$ and $R^2$ respectively represent lower alkyl.

2. A compound according to claim 1, namely ethyl O-methoxycarbonyl-2-methoxy-1-naphthohydroxamate.

3. A compound according to claim 1, namely ethyl O-ethoxycarbonyl-2-methoxy-1-naphthohydroxamate.

4. A compound according to claim 1, namely ethyl O-propoxycarbonyl-2-methoxy-1-naphthohydroxamate.

5. A compound according to claim 1, namely ethyl O-isopropoxycarbonyl-2-methoxy-1-naphthohydroxamate.

6. A compound according to claim 1, namely ethyl O-butoxycarbonyl-2-methoxy-1-naphthohydroxamate.

7. A compound according to claim 1, namely ethyl O-isobutoxycarbonyl-2-methoxy-1-naphthohydroxamate.

8. A compound according to claim 1, namely ethyl O-sec-butoxycarbonyl-2-methoxy-1-naphthohydroxamate.

9. A compound according to claim 1, namely ethyl O-pentyloxycarbonyl-2-methoxy-1-naphthohydroxamate.

10. A compound according to claim 1, namely ethyl O-hexyloxycarbonyl-2-methyl-1-naphthoxamate.

11. A compound according to claim 1, namely ethyl O-heptyloxycarbonyl-2-methoxy-1-naphthohydroxamate.

12. A compound according to claim 1, namely ethyl O-octyloxycarbonyl-2-methoxy-1-naphthohydroxamate.

13. A compound according to claim 1, namely propenyl O-isopropoxycarbonyl-2-methoxy-1-naphthohydroxamate.

14. A miticide containing as its active ingredient a miticidally effective amount of one or more of the compounds represented by the formula

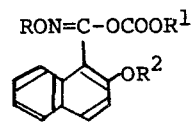

wherein R represents lower alkyl or lower alkenyl and $R^1$ and $R^2$ respectively represent lower alkyl.

* * * * *